(12) United States Patent
Huffman et al.

(10) Patent No.: US 12,352,717 B2
(45) Date of Patent: Jul. 8, 2025

(54) CAPACITANCE-BASED HUMIDITY AND GAS SENSING RFID TAGS

(71) Applicant: Temptime Corporation, Morris Plains, NJ (US)

(72) Inventors: Brian S. Huffman, Belle Mead, NJ (US); Deniz Boyu, Dover, NJ (US); Thi N. Do, West Orange, NJ (US); Mohannad Abdo, Clifton, NJ (US)

(73) Assignee: ZEBRA TECHNOLOGIES CORPORATION, Lincolnshire, IL (US)

( * ) Notice: Subject to any disclaimer, the term of this patent is extended or adjusted under 35 U.S.C. 154(b) by 152 days.

(21) Appl. No.: 17/867,031

(22) Filed: Jul. 18, 2022

(65) Prior Publication Data
US 2024/0027385 A1    Jan. 25, 2024

(51) Int. Cl.
*G01N 27/22* (2006.01)
*A61B 90/98* (2016.01)

(52) U.S. Cl.
CPC ......... *G01N 27/223* (2013.01); *G01N 27/221* (2013.01); *G01N 27/228* (2013.01); *A61B 90/98* (2016.02); *G01N 2027/222* (2013.01)

(58) Field of Classification Search
CPC .. G01N 27/223; G01N 27/221; G01N 27/228; G01N 2027/222; A61B 90/98
See application file for complete search history.

(56) References Cited

U.S. PATENT DOCUMENTS

| | | | |
|---|---|---|---|
| 3,999,946 | A | 12/1976 | Patel et al. |
| 4,228,126 | A | 10/1980 | Patel et al. |
| 4,298,348 | A | 11/1981 | Ivory |
| 4,646,066 | A | 2/1987 | Baughman et al. |
| 4,788,151 | A | 11/1988 | Preziosi et al. |

(Continued)

FOREIGN PATENT DOCUMENTS

| | | |
|---|---|---|
| CN | 103543146 | 1/2014 |
| CN | 104599956 | 5/2015 |

(Continued)

OTHER PUBLICATIONS

Search Report and Written Opinion dated Oct. 5, 2023 issued for International PCT Application No. PCT/US2023/027934.

(Continued)

*Primary Examiner* — Feba Pothen
(74) *Attorney, Agent, or Firm* — K&L Gates LLP

(57) ABSTRACT

An RFID tag system includes an antenna, an integrated circuit electrically connected to the antenna, and a humidity or gas indicator being electrically connected to the antenna and the integrated circuit. The humidity or gas indicator includes a first electrode, a second electrode, a dielectric material, and a gap between the first electrode and the second electrode. At least a portion of the gap contains the dielectric material. The dielectric material is configured to have a change in its dielectric constant responsive to exposure to an environmental stimulus, which may be at least one of humidity or the presence of a gas. The change in the dielectric constant of the dielectric material changes a capacitance of the humidity or gas indicator, causing the integrated circuit to indicate the presence of the environmental stimulus.

18 Claims, 10 Drawing Sheets

(56) References Cited

U.S. PATENT DOCUMENTS

| | | |
|---|---|---|
| 6,524,000 B1 | 2/2003 | Roth |
| 6,524,697 B1 | 2/2003 | Furuyama et al. |
| 6,642,016 B1 | 11/2003 | Sjoholm et al. |
| 6,720,866 B1 | 4/2004 | Sorrells et al. |
| 7,098,794 B2 | 8/2006 | Lindsay et al. |
| 7,503,690 B2 | 3/2009 | Song et al. |
| 7,570,169 B2 | 8/2009 | Li et al. |
| 7,604,398 B1 | 10/2009 | Akers et al. |
| 7,719,404 B2 | 5/2010 | Makela et al. |
| 8,040,243 B2 | 10/2011 | Bommer et al. |
| 8,043,000 B2 | 10/2011 | Sumida et al. |
| 8,111,143 B2 | 2/2012 | Tong et al. |
| 8,228,172 B2 | 7/2012 | Collins et al. |
| 8,267,576 B2 | 9/2012 | Haarer et al. |
| 8,357,958 B2 | 1/2013 | Cummins |
| 8,395,521 B2 | 3/2013 | Kauffman et al. |
| 8,870,082 B2 | 10/2014 | Cattaneo et al. |
| 8,899,829 B1 | 12/2014 | Butera et al. |
| 8,968,662 B2 | 3/2015 | Haarer et al. |
| 9,011,794 B2 | 4/2015 | Haarer et al. |
| 9,164,052 B1 * | 10/2015 | Speer .................. G01N 27/045 |
| 9,195,925 B2 | 11/2015 | Potyrailo et al. |
| 9,436,853 B1 | 9/2016 | Meyers |
| 9,494,032 B2 | 11/2016 | Roberson et al. |
| 9,546,911 B2 | 1/2017 | Huffman et al. |
| 9,581,501 B2 | 2/2017 | Kozono et al. |
| 10,184,777 B2 | 1/2019 | Okojie |
| 10,338,537 B2 | 7/2019 | Braunberger |
| 2003/0053377 A1 | 3/2003 | Spevacek |
| 2004/0061655 A1 | 4/2004 | Forster et al. |
| 2006/0261946 A1 | 11/2006 | Himberger et al. |
| 2007/0210923 A1 | 9/2007 | Butler et al. |
| 2008/0012580 A1 | 1/2008 | Funo et al. |
| 2008/0078233 A1 * | 4/2008 | Larson ................. G01N 29/022 |
| | | 73/335.03 |
| 2008/0292507 A1 | 11/2008 | Dee et al. |
| 2009/0010304 A1 | 1/2009 | Skinner et al. |
| 2009/0066516 A1 | 3/2009 | Lazo |
| 2009/0131718 A1 | 5/2009 | Baughman et al. |
| 2010/0001745 A1 | 1/2010 | Sumida et al. |
| 2010/0090802 A1 | 4/2010 | Nilsson et al. |
| 2010/0123583 A1 | 5/2010 | Bommer et al. |
| 2011/0211612 A1 | 9/2011 | Branecky |
| 2012/0260728 A1 | 10/2012 | Bhattacharyya et al. |
| 2013/0033364 A1 | 2/2013 | Raz et al. |
| 2013/0224875 A1 | 8/2013 | Haarer et al. |
| 2014/0004618 A1 | 1/2014 | Chien et al. |
| 2014/0144366 A1 | 5/2014 | Huffman et al. |
| 2014/0148095 A1 | 5/2014 | Smith et al. |
| 2014/0154808 A1 | 6/2014 | Patel |
| 2014/0358099 A1 | 12/2014 | Durgin et al. |
| 2015/0116093 A1 | 4/2015 | Swager et al. |
| 2016/0011157 A1 | 1/2016 | Smyth et al. |
| 2016/0261005 A1 * | 9/2016 | Rustomji ................. C25D 3/44 |
| 2016/0349224 A1 | 12/2016 | Patel et al. |
| 2017/0038325 A1 | 2/2017 | Takashima et al. |
| 2017/0211992 A1 | 7/2017 | Yeager et al. |
| 2017/0255854 A1 | 9/2017 | Bhatia et al. |
| 2017/0370692 A1 | 12/2017 | Okojie |
| 2018/0100807 A1 | 4/2018 | Abdo et al. |
| 2018/0372663 A1 * | 12/2018 | Gontard ............. G01N 33/0047 |
| 2019/0302047 A1 * | 10/2019 | Park ..................... G01N 27/045 |
| 2020/0011827 A1 * | 1/2020 | Zhou .................... G01N 27/226 |
| 2020/0193258 A1 | 6/2020 | Hawwa et al. |
| 2020/0210801 A1 * | 7/2020 | Oda ................. G06K 19/07788 |
| 2021/0109053 A1 | 4/2021 | Shiraki |
| 2022/0268640 A1 | 8/2022 | Bhatia et al. |

FOREIGN PATENT DOCUMENTS

| | | | |
|---|---|---|---|
| DE | 10 2005 061249 | 6/2007 | |
| EP | 3168608 | 5/2017 | |
| EP | 3845895 A1 * | 7/2021 | .......... G01N 27/228 |
| JP | 5723474 | 5/2015 | |
| KR | 101519317 | 5/2015 | |
| WO | WO03/044521 | 5/2003 | |
| WO | WO 20080127044 | 10/2008 | |
| WO | WO 2010/105811 | 9/2010 | |
| WO | WO2013170273 | 11/2013 | |
| WO | WO 2013/186782 | 12/2013 | |
| WO | WO2014113247 | 10/2014 | |
| WO | WO2015113086 | 8/2015 | |
| WO | WO2017151731 | 9/2017 | |
| WO | WO2020231921 | 11/2020 | |

OTHER PUBLICATIONS

Wegner et al. "Topochemical Reactions of Monomers with Conjugated Triple Bonds" 9 J. Poly. Sci.B.Poly.Letters 133-44 (1971).

Wegner "Topochemical Polymerization of Monomers with Conjugated Triple Bonds", 154 Die Makromoleculare Chemie 35-48 (1972).

World Health Organization: Vaccine Vial Monitors: FAQs. 2011. https://www.who.int/immunization/programmes_systems/supply_chain/optimize/vaccine_vial_monitors_faqs.pdf?ua=1 (Year: 2011).

I. Gascon, J.D. Marty, T. Gharsa and C. Mingotaud, 2005. "Formation of Gold Nanoparticles in a Side-Chain Linqud Crystalline Network: Influence of the Structure and Macroscopic Order of the Material Chem. Mater. 2005, 17, 21, 5228-5230" (Year: 2005).

Bhattacharyya et al., "Low-Cost, Ubiquitous RFID-Tag-Antenna-Based Sensing", Proceedings of the IEEE 2010, 98, 1593-1600.

Windl et al., "Reactivatable Passive Radio-Frequency Identification Temperature Indicator", Journal of Applied Physics 117, 17C125 (2015).

Tanguy et al. "Enhanced Radio Frequency Biosensor for Food Quality Detection Using Functionalized Carbon Nanofillers", ACS Appl. Mater. Interfaces 2015, 7, 11939-11947.

Wu et al., "3D-Printed Microelectronics for Integrated Circuitry and Passive Wireless Sensors", Microsystems & Nanoengineering 1, 15013 (2015).

Wan et al., "A New Type of TTI Based on Electrochemical Pseudo Transistor", J. of Food. Engin. 168, (2016) 79-83.

Search Report and Written Opinion dated Jul. 17, 2017 issued for International PCT Application No. PCT/US17/20142.

Office Action dated Sep. 19, 2019 issued for European Patent Application No. 17760694.4.

International search report and of a written opinion dated Aug. 10, 2020 issued for International PCT Application No. PCT/US20/32340.

Office Action dated Sep. 3, 2020 issued for European Patent Application No. 17760694.4.

Office Action dated Jan. 7, 2020 issued for European Patent Application No. 17760694.4.

Office Action dated Sep. 23, 2019 issued for European Patent Application No. 17760694.4.

Office Action dated Nov. 4, 2020 issued for Chinese Patent Application No. 201780014268.2.

Office Action dated Feb. 25, 2021 issued for Korean Patent Application No. 10-2018-7026541.

Moisture-Detecting UHF RFID Labels. Brady, webpage capture, printed Oct. 9, 2024. https://www.bradyid.com/rfid-labels-tags/moisture-detecting-uhf-rfid-labels-pid-tht-uhf-b423-42x85#overview.

* cited by examiner

US 12,352,717 B2

CAPACITANCE-BASED HUMIDITY AND GAS SENSING RFID TAGS

BACKGROUND

Many commercial products are sensitive to overly high or low humidity or the presence of certain gases (e.g., oxygen, ammonia, etc.). Exposure to such high or low humidity or gas concentrations, and/or extended periods of time at elevated humidity or gas levels may cause a product to spoil or lose efficacy/quality. The presence of certain toxic gas may even pose a threat to life and property. The conditions of the commercial products can be monitored by detecting the presence of certain gas. There is a continued need for an environmental humidity or gas indicator to detect such exposure.

Radio frequency identification (RFID) tags are commonly used to label and track products. The RFID tags may include an antenna and transmit information at predetermined frequencies when interrogated by radio transmitter/receiver. These tags may be active, with their own power, or passive and powered by the radio transmission of the interrogating device.

SUMMARY

The present disclosure provides new and innovative humidity or gas indicators and systems for providing an indication of exposure to humidity or gas changes and/or the presence thereof. In some examples, a radio frequency identification (RFID) tag system may include an antenna, an integrated circuit electrically connected to the antenna, and a humidity or gas indicator being electrically connected to the antenna and the integrated circuit. The humidity or gas indicator may include a first electrode, a second electrode, a dielectric material, and a gap between the first electrode and the second electrode. At least a portion of the gap may contain the dielectric material. The dielectric material may be configured to have a change in its dielectric constant responsive to exposure to an environmental stimulus, which may be at least one of humidity or the presence of a gas. The change in the dielectric constant of the dielectric material may change a capacitance of the humidity or gas indicator, causing the integrated circuit to indicate the presence of the environmental stimulus.

Additional features and advantages of the disclosed systems are described in, and will be apparent from, the following Detailed Description and the Figures.

DETAILED DESCRIPTION OF EXAMPLE EMBODIMENTS

Figure 1:
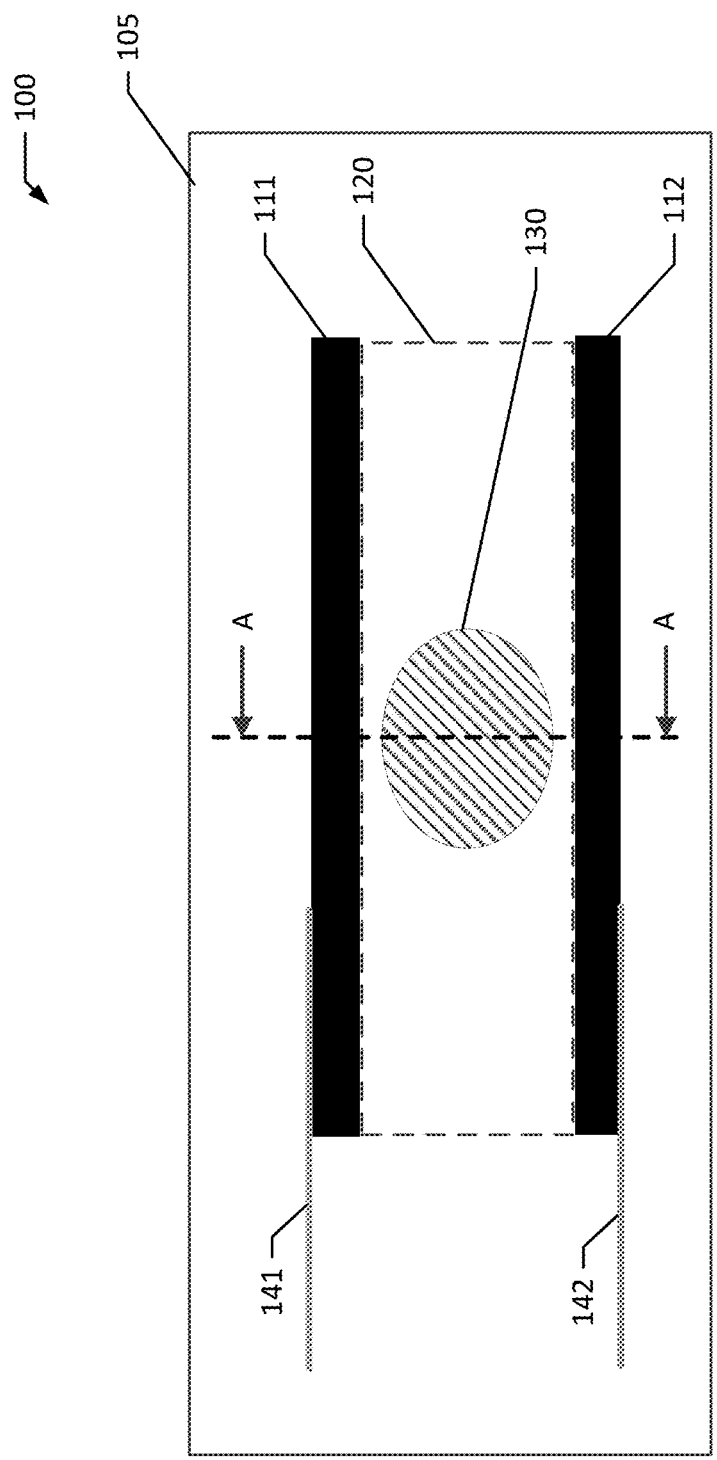
FIG. 1 is a diagram of a humidity or gas indicator according to an example embodiment of the present disclosure.

Many products, e.g., foodstuffs, flowers, concrete, batteries, vaccines, drugs, and other products may be humidity- or gas-sensitive, or perishable, and can lose quality with time at rates that are strongly influenced by the humidity or gas level. The presence of certain toxic gas may even pose a threat to life and property. The conditions of the commercial products can also be monitored by detecting a gas level, which may be generated by the products themselves as the products age or diminish in quality To detect such undesirable environmental conditions or abnormal conditions of the products, a humidity or gas indicator can be associated with the foodstuffs, flowers, concrete, batteries, or other host products to provide an alert to a health worker, or other end-user, that the products may have lost potency and possibly should not be used. The humidity or gas indicator can be also associated with a human space (e.g., house, office, school, hospital, factory, laboratory, sports stadium) to alert the user of the space about undesirable or dangerous environmental conditions.

It may be desirable to have an indicator that reports historical exposure to humidity or a gas, e.g., whether the product or space has been exposed to the humidity or gas above or below a threshold humidity or gas level, or whether the product or space has been exposed above a threshold for more than a particular amount of time, or the cumulative amount of exposure (time-exposure product) over time. In other situations, it may be desirable to have an indicator that reports the current humidity or gas level. These indicators may be provided in a variety of forms, e.g., optically readable indicators. In other cases, either alone or in combination with such optical indicators, indicators that signal historical or current humidity or gas levels with either an electrical signal or a radio signal, such as a signal provided by an RFID tag may be provided. The implementation of such electrical or radio indicators may be facilitated by the use of capacitors or other electrical components that significantly change capacitance or other electrical property in response to exposure to humidity or a gas above or below a threshold. In some cases, the response may be irreversible, i.e., the changed electrical property may not return to its original value after the threshold exposure ends. In other cases, the response may be reversible, i.e., the changed electrical property may return to its original value after the threshold exposure ends, either immediately, almost immediately, or after some period of delay.

Environmental sensing for the humidity or gas level may have many applications. For example, aspects of the present disclosure may provide an on-demand humidity/gas threshold response indicator that may ensure proper storage and shipment of products so that the products are not damaged due to inadequate environmental controls (e.g., high humidity or improper gas concentration). Using the humidity or gas sensors, various safety-related conditions may also be checked, such as electrolyte leakage in batteries, food decay during storage and/or transport, hazardous/toxic emissions during materials processing, and volatile organic compounds.

One major application of the present disclosure may be food safety, where 1.4 billion tons of food are wasted globally every year. Food items are often discarded based on a sell-by date that does not reflect the quality of the food. In situations where food is improperly handled or stored or where it is still fresh past its sell-by date, waste can be significantly reduced with a better method in food safety monitoring. Aspects of the present disclosure may be able to detect possible food spoilage in the form of methane and ammonia gases and provide customers and businesses the ability to verify the food quality while reducing financial and environmental waste.

Aspects of the present disclosure may be used in battery applications that are common in automotive, electronic, and manufacturing industries, among many more. Swelling and electrolyte leakage may be a common failure mode for batteries that often occur simultaneously. Aspects of the present disclosure may provide an RFID tag system that can be used with a battery to monitor these failure modes (e.g., incorporating the tag within the battery encasing). In some examples, this tag may be passive so it requires no power from the battery itself but can include a dielectric material that changes electrical properties in the presence of electrolyte gas. Aspects of the present disclosure may ensure that the monitored battery is in working condition with no potential for explosion or release of harmful gases.

FIG. 1 depicts an example humidity or gas indicator 100 in accordance with one or more aspects of the present disclosure. The humidity or gas indicator 100 may include a first electrode 111, a second electrode 112, a gap 120 between the first electrode 111 and the second electrode 112, and a dielectric material 130. In some examples, the first electrode 111 may be connected to a first contact terminal 141, and the second electrode 112 may be connected to a second contact terminal 142. In some examples, the first electrode 111 and the second electrode 112 may be made with metal (e.g., copper, aluminum, silver, gold), graphite, conductive polymers, or any other suitable conducting materials.

As used herein, the gap 120 may refer to a space (which may contain a dielectric material) formed between the first electrode 111 and the second electrode 112. The first electrode 111, the second electrode 112, and the gap 120 may form a capacitor, and any change to the dielectric constant of the gap 120 can affect the capacitance of the capacitor. In some examples, the width of the gap 120 (e.g., the distance between the first electrode 111 and the second electrode 112) may be at least 50% of the length of the first/second electrode 111/112, for example, at least 60%, at least 70%, at least 80%, at least or at least 100%. In other examples, the width of the gap 120 may be less than 50% of the length of the first/second electrode 111/112 or more than 100% of the length of the first/second electrode 111/112.

In some examples, a substrate 105 may be provided, and the humidity or gas indicator 100 may be disposed on or in the substrate 105. In some examples, the substrate 105 may be made with a paper or polyethylene terephthalate (PET). In other examples, the substrate 105 may be made with any other suitable non-conductive material or any breathable film, such as cloth or plastic (e.g., polyethylene terephthalate (PET), polyvinyl chloride (PVC), polyvinyl acetate (PVAC), etc.). The substrate may also be the surface of a package for a product to be monitored, e.g., incorporating the feature directly in a box or other packing container, or a label material, e.g., an adhesive backed label that may be applied to a package or product.

In some examples, at least a portion of the gap 120 may contain the dielectric material 130. In some examples, the dielectric material 130 may fill the entire gap 120, e.g., by covering the portion of the substrate between the two electrodes with a material approximately the same thickness as the electrodes. In other examples, the dielectric material 130 may fill only a portion of the gap 120. In some examples, the portion (e.g., an area) of the gap 120 filled by the dielectric material 130 may be less than 30% of the total size of the humidity or gas indicator 100 (e.g., the size of the gap 120). For example, the portion of the gap 120 filled by the dielectric material 130 may be in a range of about 5% to about 10%, about 10% to about 15%, about 15% to about 20%, about 20% to about 25%, or about 25% to about 30% of the total area of the gap 120. In this case, aspects of the present disclosure may be able to detect the change in the humidity or gas level while using a lesser/minimum amount of the dielectric material, thereby saving the product cost, particularly since, as discussed below the dielectric material may be a material with particular, finely tuned properties to reflect environmental exposure.

In other examples, the portion (e.g., area) of the gap 120 covered/filled by the dielectric material 130 may be more than 30%, for example, about 30% to about 35%, about 35% to about 40%, about 40% to about 45%, about 45% to about 50%, or about 50% to about 100% (of the total size/area of the gap 120).

The dielectric material 130 may be configured to have a change in its dielectric constant responsive to exposure to an environmental stimulus. The environmental stimulus may be at least one of humidity or the presence of a particular gas and/or the gas concentration of a particular gas. The change in the dielectric constant of the dielectric material 130 may change a capacitance of the humidity or gas indicator 100. When the humidity or gas indicator 100 is associated with an RFID tag system, this may cause an integrated circuit of the RFID tag system to indicate the presence and/or level of the environmental stimulus.

In some examples, the humidity or gas indicator 100 may be configured to change a capacitance value thereof in response to both the change in humidity and the change in gas concentration. For example, a single humidity or gas indicator 100 may be configured to detect both the change in humidity and the change in gas concentration at the same time. In other examples, the humidity or gas indicator 100 may be configured to change a capacitance value thereof in response to only one of the change in humidity and the change in gas concentration. That is, in this case, the humidity or gas indicator 100 may be configured to detect only one of the change in humidity and the change in gas concentration.

In some examples, the dielectric material 130 may include a material including at least one of polyol polymers, neutralized polymers, or any combinations thereof. In particular, in some examples, the dielectric material 130 may include at least one of hydrophilic and hygroscopic materials. For example, the dielectric material 130 may include a material including at least one of PVA, PVP, PEG, acrylics (e.g., neutralized polyacrylate), water-reducible epoxy, cellulose, water-soluble gum, PEG, hydrochromic ink, or any combinations thereof. In other examples, the dielectric material 130 may be made with any other suitable non-conductive material that changes its dielectric constant in response to exposure to the environmental stimulus, e.g., humidity or concentration of a particular gas. In some examples, the above-discussed dielectric materials may further include other additional materials, such as potassium hydroxide (KOH) and/or isopropyl alcohol (IPA). Examples of the dielectric material 130 that may be useful for detecting humidity may include polyamide, PMMA, PHEMA, cellulose and graphene. Examples of the dielectric material 130 that may be useful for detecting gases may include cellulose, zeolite, ZnO, $TiO_2$, and $SnO_2$.

In some examples, when the dielectric material 130 fills only a portion of the gap 120, the remaining space in the gap 120 may be filled with other filler material or component, including air, silicon dioxide, or any other suitable non-conductive material. In some examples, the filler material or component may be stable (e.g., tend not to change its dielectric constant) in response to the change in the environmental conditions (e.g., humidity, gas, temperature). In some examples, the change in the dielectric constant of the dielectric material 130 (and/or the change in the capacitance value of the humidity or gas indicator 100 due to this dielectric constant change) may be at least one or several orders of magnitude higher than the change in the dielectric constant of the filler material or component in the remaining space of the gap 120 (and/or the change in the capacitance value of the humidity or gas indicator 100 due to this dielectric constant change of the filler material). In some examples, the substrate 105 may be etched and the electrodes 111, 112 may be placed in the etched channels so that the substrate itself can be used as the dielectric material 130.

In some examples, the change in capacitance of the humidity or gas indicator 100 is irreversible. That is, after the humidity or gas indicator 100 was exposed to a high humidity or gas level (e.g., 75% relative humidity (RH)), although it returns to an initial humidity or gas level (e.g., from 75% RH to 40% RH), the humidity or gas indicator 100 may retain the changed capacitance value (e.g., measured at 75% RH) or may not return to its initial capacitance value (e.g., measured at 40% RH before the exposure to the high humidity or gas level). In such examples, the dielectric material 130 may be undergoing a one way or irreversible change in response to the environmental stimulus, e.g., an irreversible chemical reaction with the detected gas, or a conversion from a crystalline to an amorphous structure in response water from high humidity.

In some examples, the change in capacitance may be considered irreversible when the changed capacitance persists or does not return to its initial capacitance value after exposure for at least 48 hours to the initial humidity or gas level, such as after exposure for at least 72 hours to the initial humidity or gas level, after exposure for at least 120 hours to the initial humidity or gas level, or after exposure for at least 168 hours to the initial humidity or gas level.

In some examples, the change in capacitance of the humidity or gas indicator 100 is reversible. That is, after the humidity or gas indicator 100 returns to an initial humidity or gas level, the humidity or gas indicator 100 may not retain the changed capacitance value. For example, after the humidity or gas indicator 100 returns to the initial humidity or gas level, the capacitance value of the humidity or gas indicator 100 may return to its initial capacitance value or a capacitance value close to the initial capacitance value. Where the humidity or gas indicator 100 returns to its initial capacitance value, the humidity or gas indicator 100 may operate like a current humidity or gas indicator, or where it returns to initial state more slowly as a recent humidity or gas-level excursion indicator; where humidity or gas indicator 100 does not return to its initial capacitance value, the device may operate as a historical humidity or gas-level exposure indicator.

In some cases, the change in capacitance may be considered reversible when the changed capacitance does not persist or return to the initial capacitance value after exposure for 168 hours (a week) or less to the initial humidity or gas level. For example, the subsequent exposure to the initial humidity or gas level may be for about 1 minute to about 168 hours, such as for about 1 minute to about 2 minutes, for about 2 minutes to about 5 minutes, for about 5 minutes to about 10 minutes, for about 10 minutes to about 30 minutes, for about 30 minutes to about 1 hour, for about 1 hour to about 2 hours, for about 2 hours to about 5 hours, for about 5 hours to about 10 hours, for about 10 hours to about 24 hours, for about 24 hours to about 48 hours, for about 48 hours to about 72 hours, for about 72 hours to about 120 hours, or for about 120 hours to about 168 hours.

In some examples, the change in capacitance of the humidity or gas indicator 100 may occur after its exposure to a change in humidity or gas concentration above a first threshold change value for a first predetermined amount of time. In some examples, the change in capacitance of the humidity or gas indicator 100 may occur after its exposure to a change in humidity or gas concentration below a second threshold change value for a second predetermined amount of time. The second predetermined amount of time will be described in more detail below.

In some examples, the first or second threshold change value may be in a range of about 0.1% to 1% change in humidity, about 1% to 2% change in humidity, about 2% to 3% change in humidity, about 3% to 5% change in humidity, or any combinations thereof. In some examples, the first or second threshold change value may be at least a certain level of the gas concentration, for example, at least 10 ppm or above of a target gas, at least 50 ppm or above of a target gas, or at least 100 ppm or above of a target gas.

In some examples, the change in capacitance value of the humidity or gas indicator 100 may occur almost immediately or after a relatively short time period of exposure to a change in humidity or gas concentration. In such cases, the change in capacitance value can occur after exposure for about 60 seconds or less, such as for about seconds or less, for about 0 seconds or less, for about 30 seconds or less, for about 20 seconds or less, for about 15 seconds or less, for about 10 seconds or less, for about 5 seconds or less, or for about 2 seconds or less. The first and/or second predetermined amount of time may be also in this time range.

In some cases, the change in capacitance value may occur after a relatively longer time period of exposure of the humidity or gas indicator 100 to the humidity or gas level above (or below) the threshold humidity or gas level (e.g., the first/second threshold change value). In such cases, the change in capacitance value may occur after exposure of the humidity or gas indicator 100 for about 1 minute to about 72 hours to the humidity or gas level above (or below) the threshold humidity or gas level, such as for about 1 minute to about 2 minutes, for about 2 minutes to about 5 minutes, for about 5 minutes to about 10 minutes, for about 10 minutes to about 30 minutes, for about 30 minutes to about 1 hour, for about 1 hour to about 2 hours, for about 2 hours to about 5 hours, for about 5 hours to about hours, for about 10 hours to about 24 hours, for about 24 hours to about 48 hours, or for about 48 hours to about 72 hours. The first and/or second predetermined amount of time may be also in this time range. With a longer times to change property in response to a humidity or gas-level excursion above the threshold, the humidity or gas indicator 100 may be used as a time-humidity/gas-level exposure indicator.

In some examples, the capacitance of the humidity or gas indicator 100 may change continuously as the humidity or gas level changes. Therefore, at different humidity or gas concentration levels, a capacitance value curve (e.g., linear curve, power curve, logarithmic curve) can be developed. The types of curve may be determined based on the types of the dielectric material used in the humidity or gas indicator. This curve can be used to match the measured capacitance value to a corresponding humidity or gas concentration.

In some examples, the dielectric material 130 may be configured to change color after exposure to above or below a certain threshold humidity or gas level for a predetermined amount of time or less (e.g., the above first or second predetermined amount of time). In this way, the user of the humidity or gas indicator can be notified about the change in humidity or gas level without having to use any separate tool (e.g., RFID reader). In response to being notified about the change, the user may try to use a separate tool to obtain more accurate information about the change in the humidity or gas level (e.g., current humidity or gas level, historical curve, exposure time).

In some examples, the dielectric material 130 may include a color-changing ink (e.g., diacetylene). The color change may include at least one of a change in color, color density, fluorescence, or opacity. In some examples, the color change of the dielectric material 130 may be irreversible. In other examples, the color change of the dielectric material 130 may be reversible.

In some examples, the length of the first/second electrode 111/112 may be about 0.5 to 3 inches. In other examples, the first/second electrode 111/112 may have any other suitable length. In some examples, the thickness of the first/second electrode 111/112 may be about 1 to about 5 mil, about 5 to about 15 mil, about 15 to about 50 mil, or about to about 100 mil. In other examples, the first/second electrode 111/112 may have any other suitable thickness.

In some examples, the length of the dielectric material 130 may be about 0.1 to 3 inches. In other examples, the first/second electrode 111/112 may have any other suitable length. In some examples, the thickness of the dielectric material 130 may be about to about 0.5 mil, about 0.5 to about 1.5 mil, about 1.5 to about 5.0 mil, or about 5.0 to about 10.0 mil. In other examples, the dielectric material 130 may have any other suitable thickness.

Figure 2:
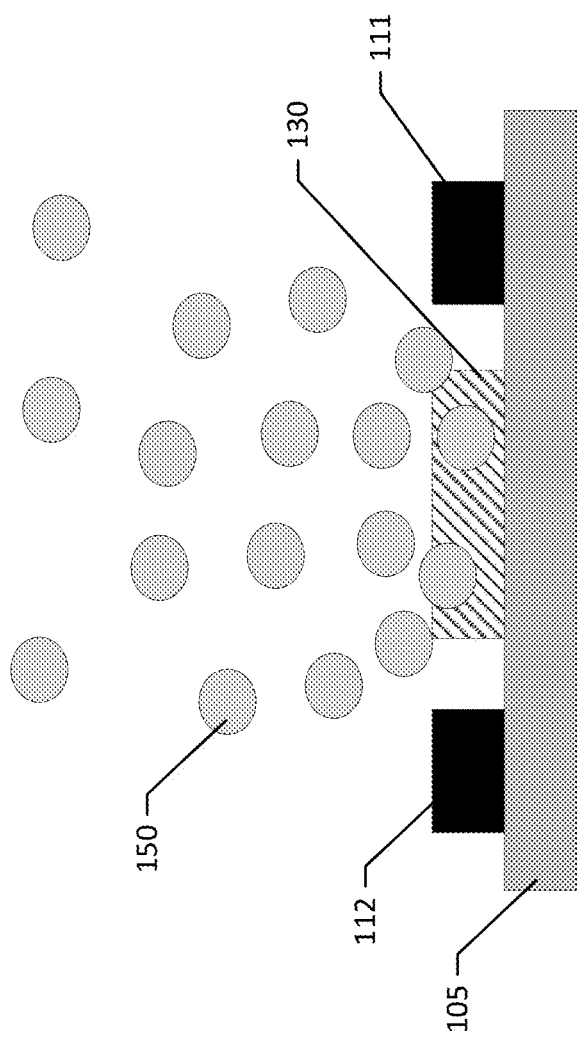
FIG. 2 is a cross-sectional view of the humidity or gas indicator of FIG. 1 along the line of A-A with the presence of some humidity.

FIG. 2 is a cross-sectional view of the humidity or gas indicator 100 of FIG. 1 along the line of A-A with the presence of some humidity. As shown in FIG. 2, the dielectric material 130 disposed between the first and second electrodes 111, 112 may attract or absorb moisture/water molecules 150. The dielectric material 130 may have the ability to retain the moisture/water molecules 150 after being exposed to certain level of humidity for a certain period of time. Not wishing to be bound by theory, it is believed that after exposure to a certain humidity level for a sufficient period of time, the dielectric material 130 may allow the moisture/water molecules 150 to form hydrogen bonds, increasing the electrical (e.g., capacitance) properties of the humidity or gas indicator 100 as more polar molecules are introduced into the dielectric material 130. For example, as the dielectric material 130 attracts or absorbs moisture/water molecules 150, the electron charges stored therein may increase, changing the dielectric constant of the material, which may increase the capacitance of the humidity or gas indicator 100. Therefore, as the humidity increases, the capacitance of the humidity or gas indicator 100 may also increase.

Figure 3:
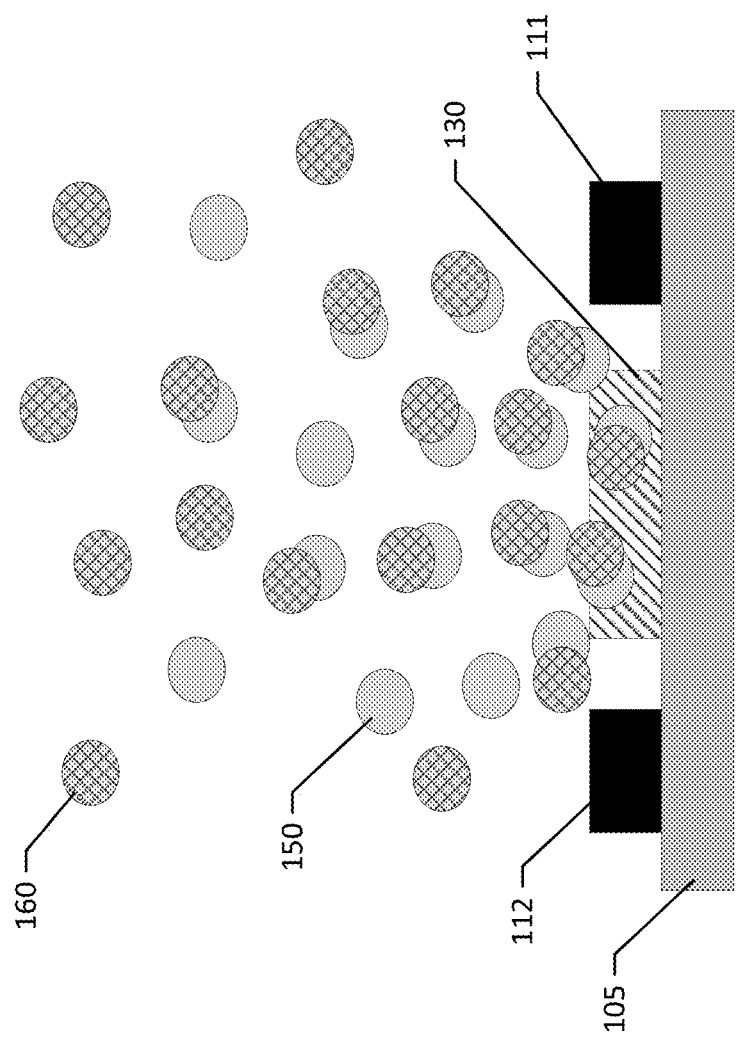
FIG. 3 is a cross-sectional view of the humidity or gas indicator of FIG. 1 along the line of A-A with the presence of some humidity and gas.

FIG. 3 is a cross-sectional view of the humidity or gas indicator 100 of FIG. 1 along the line of A-A with the presence of some humidity and gas. As shown in FIG. 3, the dielectric material 130 disposed between the first and second electrodes 111, 112 may also attract or absorb gas molecules 160. Examples of the gas molecules 160 may include gasses emitted during electrolyte decomposition (hereinafter "electrolyte gas"), ammonia, carbon monoxide, or methane. Examples of the electrolyte gas may include hydrogen fluoride (HF), $CO_2$, CO, and $H_2$ gases that may be released as a result of electrolyte decomposition. The dielectric material 130 may have the ability to retain the gas molecules 160 after being exposed to a certain level of gas concentration for a certain period of time. Not wishing to be bound by theory, it is believed that after exposure to a certain gas level for a sufficient period of time, the dielectric material 130 may allow the gas molecules 160 to form hydrogen bonds, increasing the electrical (e.g., capacitance) properties of the humidity or gas indicator 100 as more polar molecules are introduced into the dielectric material 130. For example, some gas molecules (e.g., ammonia) having hydrogen in the chemical structure can also form hydrogen bonds with water molecules, as both have hydrogen present in the structure, which may be ultimately attracted/bonded to the dielectric material 130. In this case, the moisture/water molecules 150 may effectively serve as a vehicle to transport the gas molecules 160 to the dielectric material 130. This may make additional changes to the capacitance of the humidity or gas indicator 100.

The ability of the dielectric material 130 to retain the water/gas molecules after being exposed to a certain level of humidity/gas concentration for a certain period of time can be tuned/altered so that the range of the detectable humidity/gas level of the humidity or gas indicator 100 can be tied to properties of a perishable product and/or target space.

In some examples, the humidity or gas indicator 100 may have a first capacitance value before exposure to the humidity or gas concentration above the threshold/target humidity or gas level, and a second capacitance value after exposure to the humidity or gas concentration above the threshold/target humidity/gas level. The second capacitance may be greater than the first capacitance. In some examples, the first capacitance value may be in a range of 5 pF to 10 pF, 10 pF to 15 pF, 15 pF to 20 pF, or any combinations thereof. In some examples, the second capacitance value may be equal to or greater than 10 pF, for example, in a range of from about 10 pF to about 20 pF, from about pF to about 50 pF, from about 50 pF to about 1000 pF, greater than about 1000 pF, or any combinations thereof. In other examples, the first and second capacitance values may have any other suitable capacitance value. In some examples, the difference between the first capacitance value and the second capacitance value may be in a range of about 2 pF to about 3000 pF, for example, from about 2 pF to about 10 pF, from about 10 pF to about pF, from about 20 pF to about 50 pF, from about 50 pF to about 100 pF, from about 100 pF to about 1000 pF, from about 1000 pF to about 3000 pF, greater than 3000 pF, or any combinations thereof.

Figure 4:
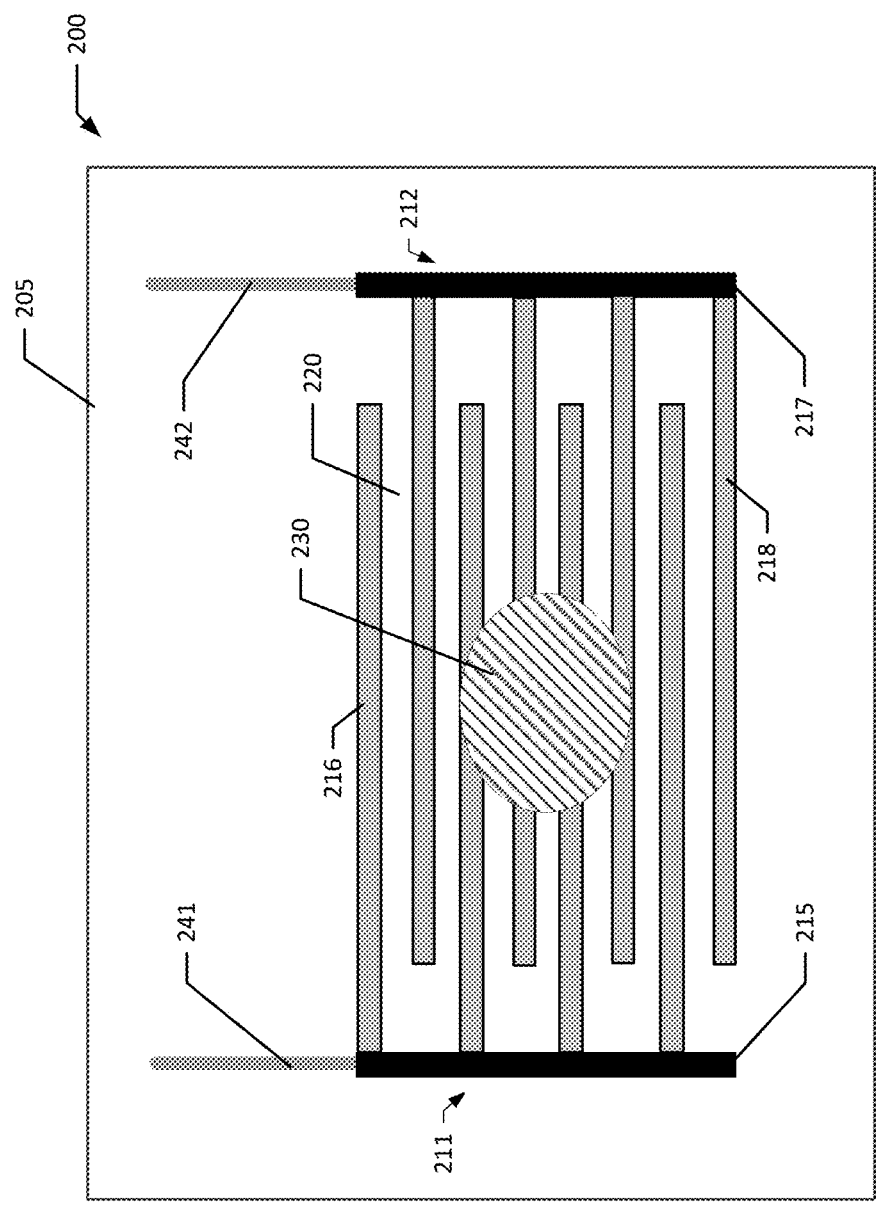
FIG. 4 is a diagram of a humidity or gas indicator according to an example embodiment of the present disclosure.
Figure 5:
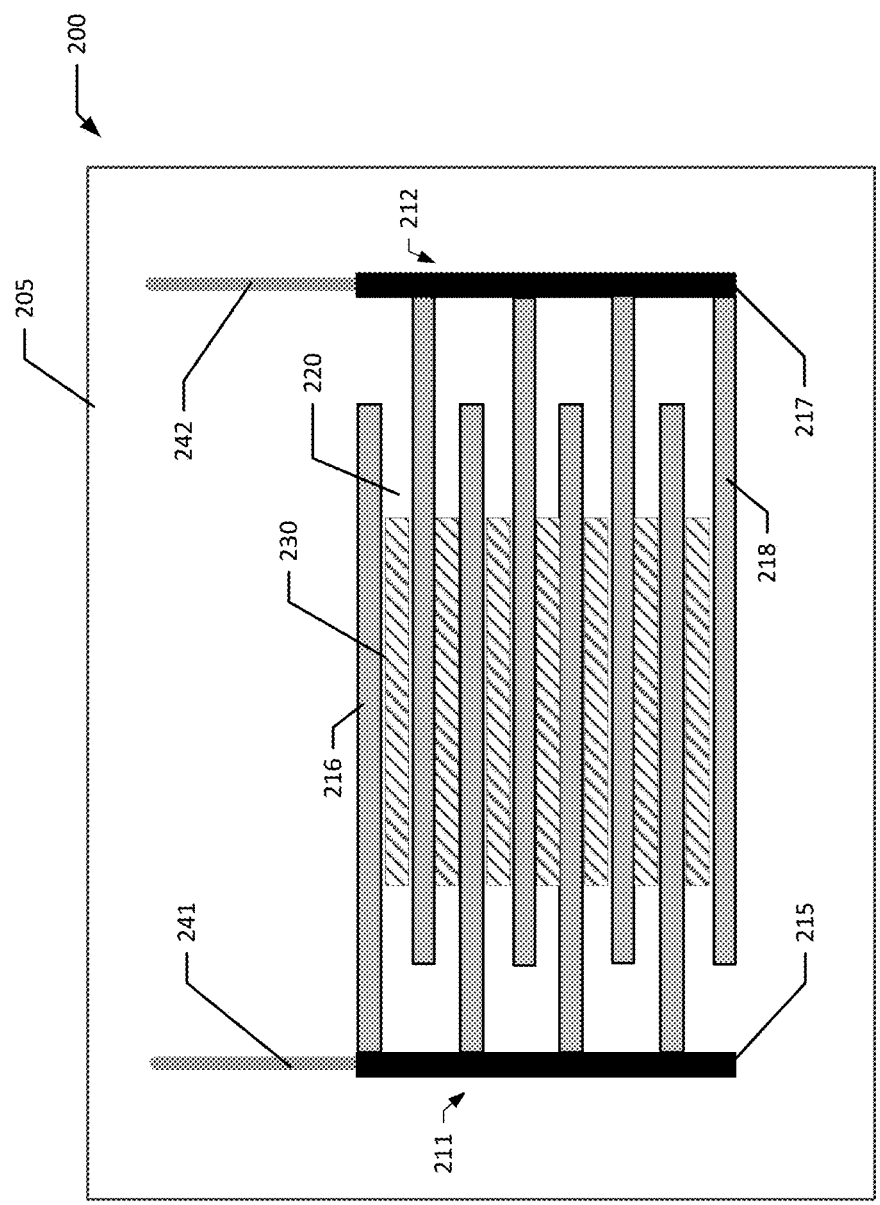
FIG. 5 is a diagram of a humidity or gas indicator according to an example embodiment of the present disclosure.

FIGS. 4 and 5 illustrate a high-level component diagram of an example humidity or gas indicator 200 according to another example embodiment of the present disclosure. The humidity or gas indicator 200 may include a first electrode 211, a second electrode 212, a gap 220 between the first electrode 211 and the second electrode 212, and a dielectric material 230. In some examples, the first electrode 211 may be connected to a first contact terminal 241, and the second electrode 212 may be connected to a second contact terminal 242. In some examples, a substrate 205 may be provided, and the humidity or gas indicator 200 may be disposed on or in the substrate 205.

In some examples, when the first electrode 211 and the second electrode 212 are in a comb shape, the gap 220 can be defined as any space between the first base plate 215 and the second base plate 217 (including the space between the first sub-electrode 216 and the second sub-electrode 218). The first electrode 211, the second electrode 212, and the gap 220 may form a capacitor, and any dielectric material in the gap 220 can affect the capacitance of the capacitor. In some examples, the width of the gap 220 (e.g., the distance between the first base plate 215 and the second base plate 217) may be at least 50% of the length of first/second base plates 215, 217, for example, at least 60%, at least 70%, at least 80%, at least 90, or at least 100%. In other examples, the width of the gap 220 may be less than 50% of the length of the first/second base plates 215, 217 or more than 100% of the length of the first/second base plates 215, 217.

In the humidity or gas indicator 200, the first electrode 211 and the second electrode 212 may be in a comb shape and interleaved with each other. For example, the first electrode 211 may include a first base plate 215 and plurality of first sub-electrodes 216 extending from the first base plate 215, and the second electrode 212 may include a second base plate 217 and plurality of second sub-electrodes 218 extending from the second base plate 217. The gap 220 may be formed between the first base plate 215 and the plurality of first sub-electrodes 216 of the first electrode 211 and the second base plate 217 and the plurality of second sub-electrodes 218 of the second electrode 212.

In some examples, at least a portion of the gap 220 may contain the dielectric material 230. In some examples, the dielectric material 230 may fill the entire gap 220. In other examples, the dielectric material 230 may fill only a portion of the gap 220. In some examples, the portion (e.g., an area) of the gap 220 filled by the dielectric material 230 may be less than 30% of the total size of the humidity or gas indicator 200 (e.g., the size of the gap 220). For example, the portion of the gap 220 filled by the dielectric material 230 may be in a range of about 5% to about 10%, about 10% to about 15%, about 15% to about 20%, about 20% to about 25%, or about 25% to about 30%. In this case, aspects of the present disclosure may be able to detect the change in the humidity or gas level while using less/minimum amount of the dielectric material, thereby saving the product cost.

In other examples, the portion of the gap 220 filled by the dielectric material 230 may be more than 30%, for example, about 30% to about 35%, about 35% to about 40%, about 40% to about 45%, about 45% to about 50%, about 50% to about 100% (of the total size of the gap 220).

In some examples, the dielectric material 230 may be disposed over some portions of the first and second electrodes 211, 212. For example, the dielectric material 230 may be disposed over some portions of the first and second sub-electrodes 216, 218 (in addition to the gap 220 between the first and second electrodes 211, 212) as shown in FIG. 4. In other examples, the dielectric material 230 may be disposed only within the gap 220 between the first and second electrodes 211, 212 without being disposed over the first and second electrodes 211, 212, as shown in FIG. 5.

In some examples, the humidity or gas indicator 200 may be configured to change a capacitance value thereof in response to both the change in humidity and the change in gas concentration. That is, the humidity or gas indicator 200 may be configured to detect both the change in humidity and the change in gas concentration at the same time. In other examples, the humidity or gas indicator 200 may be configured to change a capacitance value thereof in response to only one of the change in humidity and the change in gas concentration. That is, in this case, the humidity or gas indicator 200 may be configured to detect only one of the change in humidity and the change in gas concentration.

Other configurations/features/characteristics of the humidity or gas indicator 200 (e.g., dielectric material, filer material, threshold humidity or gas level, reversibility, color change, response time, material, size of the components, types of gas, capacitance value change) may be similar to and/or same as the ones described above with respect to the humidity or gas indicator 100 and FIGS. 1 to 3 and, thus, duplicate description may be omitted.

Figure 6:
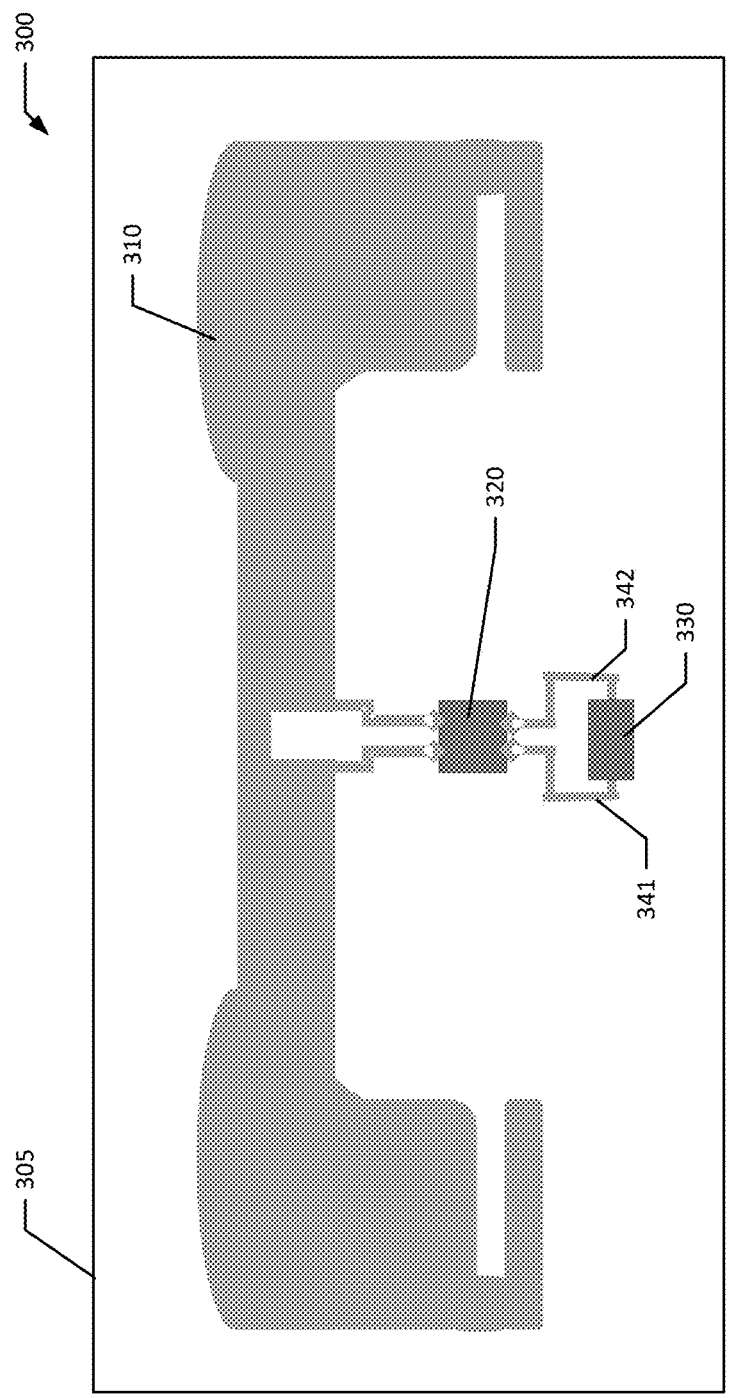
FIG. 6 is a diagram of an RFID tag system according to an example embodiment of the present disclosure.

FIG. 6 illustrates an RFID tag system 300 according to an example embodiment of the present disclosure. The RFID tag system 300 may include an antenna 310, an integrated circuit 320 electrically connected to the antenna 310, and a humidity or gas indicator 330 electrically connected to the integrated circuit 320 and the antenna 310 (e.g., through the integrated circuit 320). The humidity or gas indicator 330 may be one of the humidity or gas indicators described above (e.g., humidity or gas indicator 100 or 200). The RFID tag system 300 may further include a first contact terminal 341 connected to one side of the humidity or gas indicator 330 and a second contact terminal 342 connected to the other side of the humidity or gas indicator 330. The humidity or gas indicator 330 may be connected to the integrated circuit 320 through the first/second contact terminals 341/342. The first/second contact terminals 341/342 may be the first/second contact terminals described above (e.g., first/second contact terminals 141/142, 241/242). The RFID tag system 300 may be configured to change at least one of a frequency response, a resonant frequency, a phase response, a backscatter signal strength, and an antenna gain in response to humidity/gas exposure dependent changes to capacitance of the humidity or gas indicator 330. In some examples, the humidity or gas indicator 330 may be connected to dedicated inputs on the integrated circuit 320 to detect, for example, capacitance value/change of the humidity or gas indicator 330. This capacitance value/change of the humidity or gas indicator 330 may be transmitted by the RFID tag to the reader as data bits (along with Tag ID, etc.). In an alternative embodiment, the capacitor itself may be part of the RFID circuit, changing the frequency response of the RFID when the capacitance changes.

In some examples, the humidity or gas indicator 330 may be fully or partially printed on a rigid or flexible substrate 305, for example, by screen printing, gravure, flexographic, ink jet, or slot die coating. In other examples, the humidity or gas indicator 330 may be printed using any other suitable printing methods.

Figure 7:
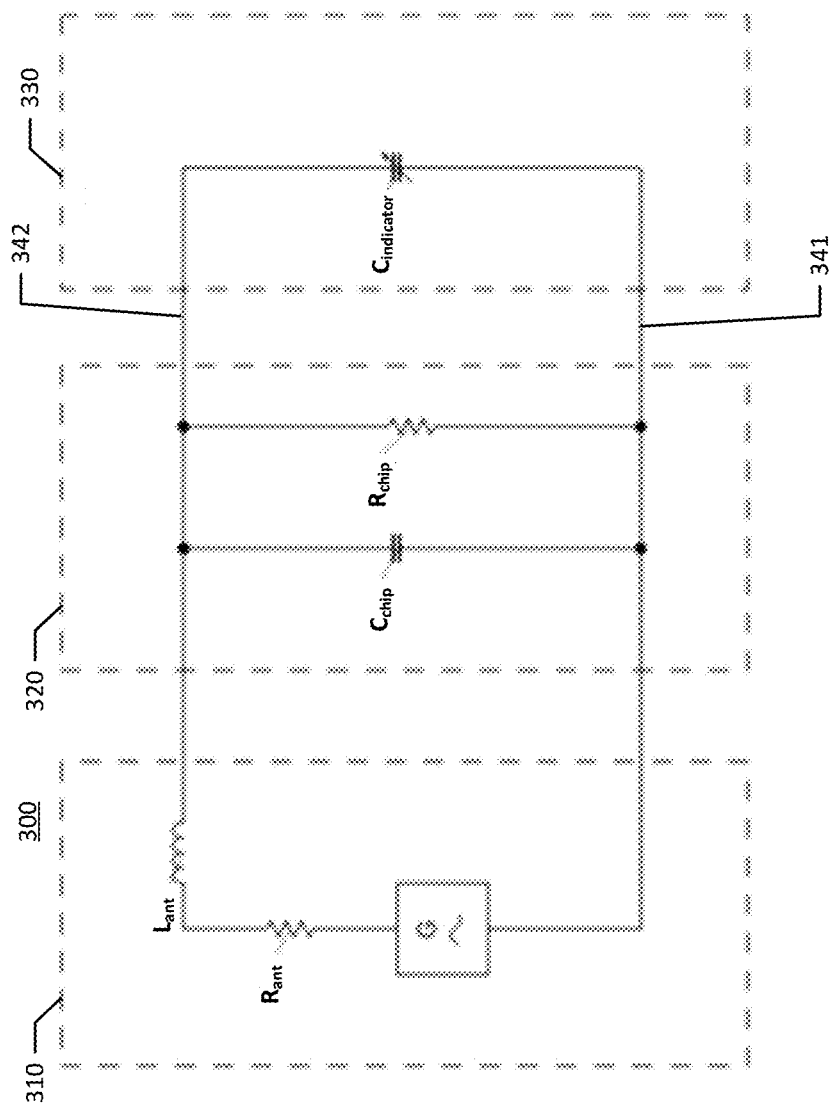
FIG. 7 is a circuit diagram of the RFID tag system of FIG. 6.

FIG. 7 illustrates a circuit diagram of the RFID tag system 300 according to an example embodiment of the present disclosure. As illustrated in FIG. 7 (and FIG. 6), the humidity or gas indicator 330 may be connected to the integrated circuit 320 and the antenna 310 in parallel. The frequency response of the RFID tag system 300 may be changed based on the threshold humidity or gas level of the humidity or gas indicator 330. For example, the threshold humidity or gas level of the humidity or gas indicator 330 may be based on the humidity or gas-dependent component (e.g., dielectric material 130, 230) and design of the circuit components and/or capacitor. In some examples, a change in capacitance of the humidity or gas indicator 330 may alter the impedance of the entire circuit in the RFID system 300, thus, changing the frequency response.

In FIG. 7, G may refer to the sinusoidal voltage generated in the RFID tag antenna 310 from a carrier wave transmitted by an RFID reader. Rant may be the resistance of the antenna 310, Lain may be the inductance of the antenna 310, $C_{chip}$ may be the RFID tag's integrated circuit capacitance, $R_{chip}$ may be the RFID tag's integrated circuit resistance, and $C_{indicator}$ may be the tunable/variable capacitance of the humidity or gas indicator 330 that changes, for example, based on the threshold humidity or gas level (and/or the change in dielectric constant) of the dielectric material of the humidity or gas indicator 330. In some examples, the change to the capacitance/resistance is reversible. In other examples, the change to the capacitance/resistance is irreversible.

The resonant frequency $f_r$ of the RFID tag system 300 may be expressed as in the following equation:

$$f_r = \frac{1}{2\pi\sqrt{L_{ant}(C_{chip} + C_{indicator})}} \quad \text{(Equation 2)}$$

The change in capacitance can be made as large or as small as needed. In some examples, the specific threshold humidity or gas level at which the change in resonant frequency is required can be designed, for example, based on selecting the appropriate material for building the humidity or gas indicator 330.

In some examples, the integrated circuit 320 may be configured to detect a capacitance value or the change in capacitance of the humidity or gas indicator 330. In some examples, the RFID tag system 300 may further include a memory configured to record information indicating the detected capacitance value/change of the humidity or gas indicator 330. In some examples, the RFID tag system 300 may further include an RFID reader configured to receive a communication from the integrated circuit 320 or the memory indicating the detected capacitance value/change in capacitance of the humidity or gas indicator 330.

In some examples, the integrated circuit 320 may be configured to detect a capacitance value/change of the humidity or gas indicator 330 equal to or greater than a first threshold capacitance value.

In some examples, the first threshold capacitance value may correspond to a first humidity value around or above 40% RH, around or above 50% RH, around or above 60% RH, around or above 70% RH, or around or above 80% RH. In some examples, the first threshold capacitance value may correspond to a first humidity value in a range of from about 40% to about 45% RH, about 45% to about 50% RH, about 50% to about 55% RH, from about 55% to about 60% RH, from about 60% to about 65% RH, from about 65% to about 70% RH, from about 70% to about 75% RH, from about 75% to about 80% RH, from about 80% to about 85% RH, from about 85% to about 90% RH, or any combinations thereof. In other examples, the first threshold capacitance value may correspond to any other suitable humidity value (e.g., between 0% RH to 40% RH).

In some examples, the first threshold capacitance value may correspond to an ammonia gas concentration value around or above 50 ppm, for example, in a range of about ppm to about 150 ppm. For example, the first threshold capacitance value may correspond to an ammonia gas concentration value from about 50 ppm to about 60 ppm, from about 60 ppm to about 70 ppm, from about 70 ppm to about 80 ppm, from about 80 ppm to about 90 ppm, from about 90 ppm to about 100 ppm, from about 100 ppm to about 110 ppm, from about 110 ppm to about 120 ppm, from about 120 ppm to about 130 ppm, from about 130 ppm to about 140 ppm, from about 140 ppm to about 150 ppm, or any combinations thereof. In other examples, the first threshold capacitance value may correspond to any other suitable ammonia gas concentration value (e.g., below 50 ppm or above 150 ppm).

In some examples, the first threshold capacitance value may correspond to a carbon monoxide gas concentration value around or above 70 ppm, for example, in a range of about 70 ppm to about 150 ppm. For example, the first threshold capacitance value may correspond to a carbon monoxide gas concentration value in a range of from about 70 ppm to about 80 ppm, from about 80 ppm to about 90 ppm, from about 90 ppm to about 100 ppm, from about 100 ppm to about 110 ppm, from about 110 ppm to about 120 ppm, from about 120 ppm to about 130 ppm, from about 130 ppm to about 140 ppm, from about 140 ppm to about 150 ppm, or any combinations thereof. In other examples, the first threshold capacitance value may correspond to any other suitable carbon monoxide gas concentration value (e.g., below 70 ppm or above 150 ppm).

In some examples, the first threshold capacitance value may correspond to an electrolyte gas concentration value around or above 50 ppm, for example, in a range of about ppm to about 2,000 ppm. For example, the first threshold capacitance value may correspond to an electrolyte gas concentration value in a range of from about 50 ppm to about 60 ppm, from about 60 ppm to about 70 ppm, from about 70 ppm to about 80 ppm, from about 80 ppm to about 90 ppm, from about 90 ppm to about 100 ppm, from about 100 ppm to about 110 ppm, from about 110 ppm to about 120 ppm, from about 120 ppm to about 130 ppm, from about 130 ppm to about 140 ppm, from about 140 ppm to about 150 ppm, from about 150 ppm to about 500 ppm, from about 500 ppm to about 1000 ppm, from about 1000 ppm to about 1500 ppm, or from about 1500 ppm to about 2000 ppm. In other examples, the first threshold capacitance value may correspond to any other suitable electrolyte gas concentration value (e.g., below 50 ppm or above 2000 ppm).

In some examples, the integrated circuit 320 may be configured to detect a capacitance value of the humidity or gas indicator 330 equal to or lower than a second threshold capacitance value.

In some examples, the second threshold capacitance value may correspond to a humidity value around or below 50% RH, or around or below 40% RH, or around or below 30% RH, or around or below 20% RH, or around or below 10% RH. In some examples, the second threshold capacitance value may correspond to a humidity value in a range of from about 10% to about 15% RH, from about 15% to about 20% RH, from about 20% to about 25% RH, from about 25% to about 30% RH, from about 30% to about 35% RH, from about 35% to about 40%, from about 40% to about 45%, from about 45% to about 50%, or any combinations thereof. In other examples, the second threshold capacitance value may correspond to any other suitable humidity value (e.g., above 50% RH).

In some examples, the second threshold capacitance value may correspond to an atmosphere with an oxygen gas concentration value around or below about 19.5% by volume. In some examples, the second threshold capacitance value may correspond to an atmosphere with an oxygen gas concentration value in a range of about 10% to about 19.5% by volume, for example, around 19.5%, from about 18% to about 19.5%, from about 16% to about 18%, from about 14% to about 16%, from about 12% to about 14%, from about 10% to about 12%, or any combinations thereof. In other examples, the second threshold capacitance value may correspond to any other suitable atmosphere with an oxygen gas concentration value above 19.5% or below 10% by volume.

In some examples, the integrated circuit 320 may be configured to transmit a notification to the RFID reader in response to detecting a capacitance value/change of the humidity or gas indicator 330 equal to or greater than the first threshold capacitance value or in response to detecting a capacitance value of the humidity or gas indicator 330 equal to or lower than the second threshold capacitance value. Examples of the notification may include "do not use," "xx % RH detected," or "xxx ppm of xxx gas detected."

In some examples, the RFID tag system 300 may further include a substrate 305. In some examples, the antenna 310, the integrated circuit 320, and/or the humidity or gas indicator 330 are disposed on or in the substrate 305. In some examples, the humidity or gas indicator 330 may be disposed on a layer different from the antenna 310 and/or the integrated circuit 320. In other examples, the humidity or gas indicator 330 may be disposed on a layer same as the antenna 310 and/or the integrated circuit 320. In some examples, the substrate 305 may be made with a paper or polyethylene terephthalate (PET). In other examples, the substrate 305 may be made with any other suitable material.

In some examples, the humidity or gas indicator 330 may change a capacitance value thereof in response to both the change in humidity and the change in gas concentration, and the integrated circuit 320 may be configured to differentiate whether the changed capacitance value is triggered (primarily) by the change in humidity or the change in gas concentration. For example, the integrated circuit 320 may determine that the changed capacitance value is triggered (primarily) by the change in humidity when the changed capacitance value is within a first range. The integrated circuit 320 may determine that the changed capacitance value is triggered (primarily) by the change in gas concentration when the changed capacitance value is within a second range. The second range may be greater than the first range. In some examples, the first range may be from about 2 pF to about pF, and the second range may be greater than 100 pF, for example, from about 100 pF to about 3000 pF.

Figure 8:
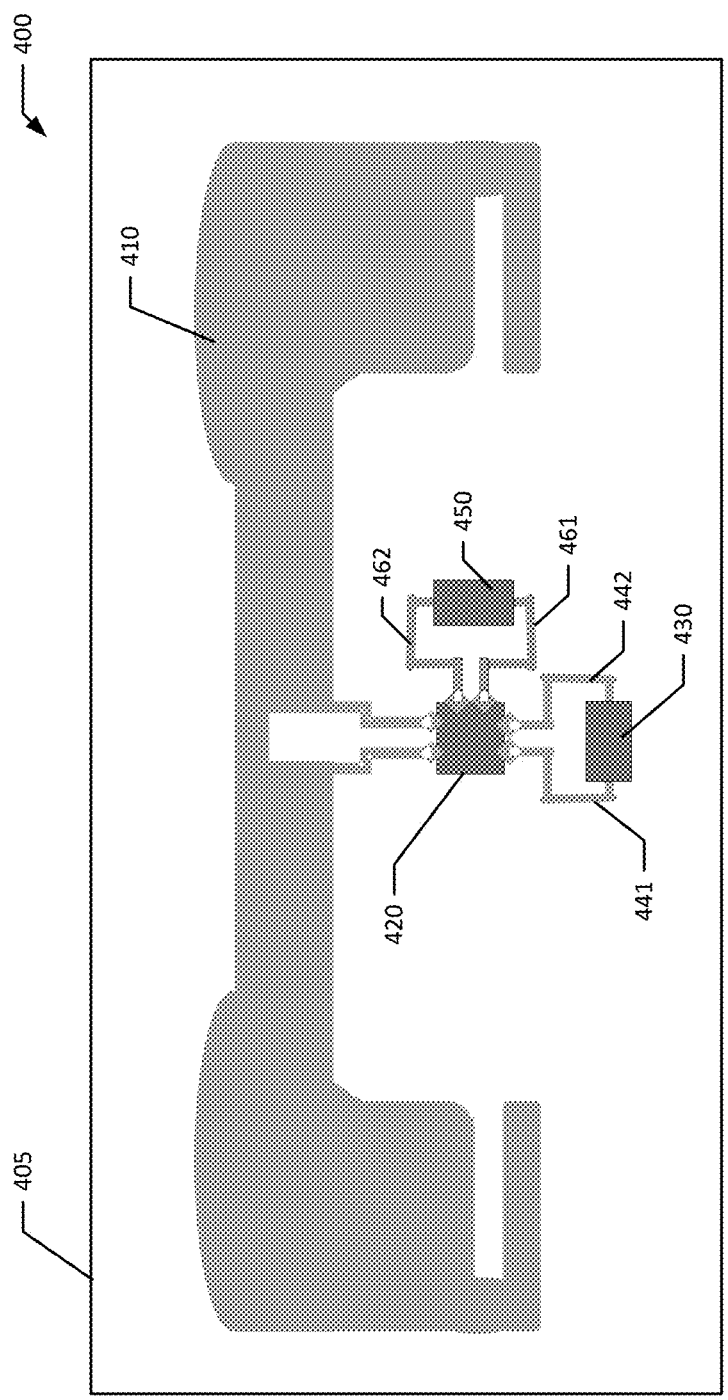
FIG. 8 is a diagram of an RFID tag system according to an example embodiment of the present disclosure.

FIG. 8 illustrates an RFID tag system 400 according to an example embodiment of the present disclosure. In this example, the RFID tag system 400 may include multiple humidity or gas indicators. The RFID tag system 400 may include an antenna 410, an integrated circuit 420 electrically connected to the antenna 410, a first humidity or gas indicator 430 and a second humidity or gas indicator 450. Both the first humidity or gas indicator 430 and the second humidity or gas indicator 450 may be electrically connected to the integrated circuit 420 and the antenna 410 (e.g., through the integrated circuit 420). The first and second humidity or gas indicators 430, 450 may be one of the humidity or gas indicators described above (e.g., humidity or gas indicator 100, 200, 330).

The RFID tag system 400 may further include a first contact terminal 441 connected to one side of the first humidity or gas indicator 430 and a second contact terminal 442 connected to the other side of the first humidity or gas indicator 430. The first humidity or gas indicator 430 may be connected to the integrated circuit 420 through the first/ second contact terminals 441/442. The RFID tag system 400 may further include a third contact terminal 461 connected to one side of the second humidity or gas indicator 450 and a fourth contact terminal 462 connected to the other side of the second humidity or gas indicator 450. The second humidity or gas indicator 450 may be connected to the integrated circuit 420 through the third/fourth contact terminals 461/462. The first/second and third/fourth contact terminals may be the first/second contact terminals described above (e.g., first/second contact terminals 141/ 142, 241/242). The RFID tag system 400 may be configured to change at least one of a frequency response, a resonant frequency, a phase response, a backscatter signal strength, and an antenna gain in response to humidity/gas exposure-dependent changes to capacitance of the first humidity or gas indicator 430 and/or the second humidity or gas indicator 450. In some examples, the first humidity or gas indicator 430 and/or the second humidity or gas indicator 450 may be connected to dedicated inputs on the RFID integrated circuit 420 to detect, for example, capacitance value/change of the first humidity or gas indicator 430 and/or the second humidity or gas indicator 450. This capacitance value/change may be transmitted by the RFID tag to the reader as data bits (along with Tag ID, etc.). Although two humidity or gas indicators are illustrated in FIG. 8, there could be more than two humidity or gas indicators.

Other configurations/features/characteristics of the RFID tag system 400 (e.g., threshold humidity or gas level, memory, RFID reader, threshold capacitance value, types of gas) may be similar to and/or same as the ones described above with respect to RFID tag system 300 and, thus, duplicate description may be omitted.

In some examples, the first humidity or gas indicator 430 may serve primarily or only as a humidity indicator. In this case, the dielectric material of the first humidity or gas indicator 430 may have a change in its dielectric constant responsive to exposure primarily to humidity. The second humidity or gas indicator 450 may serve primarily or only as a gas indicator. In this case, the dielectric material of the second humidity or gas indicator 450 may have a change in its dielectric constant responsive to exposure primarily to the presence of gas and/or the gas concentration. In some examples, the dielectric material of the first humidity or gas indicator 430 may be different from the dielectric material of the second humidity or gas indicator 450.

In some examples, the dielectric material of the second humidity or gas indicator 450 may have a change in its dielectric constant responsive to exposure to both humidity and gas concentration. For example, the second humidity or gas indicator 450 may react to both of the high humidity and gas concentration (e.g., having a higher capacitance when both conditions exist than only one of the conditions exists). In this case, the second humidity or gas indicator 450 (primarily serving as a gas indicator) may be calibrated, for example, by the integrated circuit 420, using the first humidity or gas indicator 430 (primarily serving as a humidity indicator). For example, the RFID tag system 400 (e.g., the integrated circuit 420) may calculate the capacitance value/ change due only to the change in gas concentration by subtracting the capacitance value/change due only to the humidity, which is detected from the first humidity or gas indicator 430, from the capacitance value/change due to both the humidity and gas concentration, which is detected from the second humidity or gas indicator 450.

Figure 9:
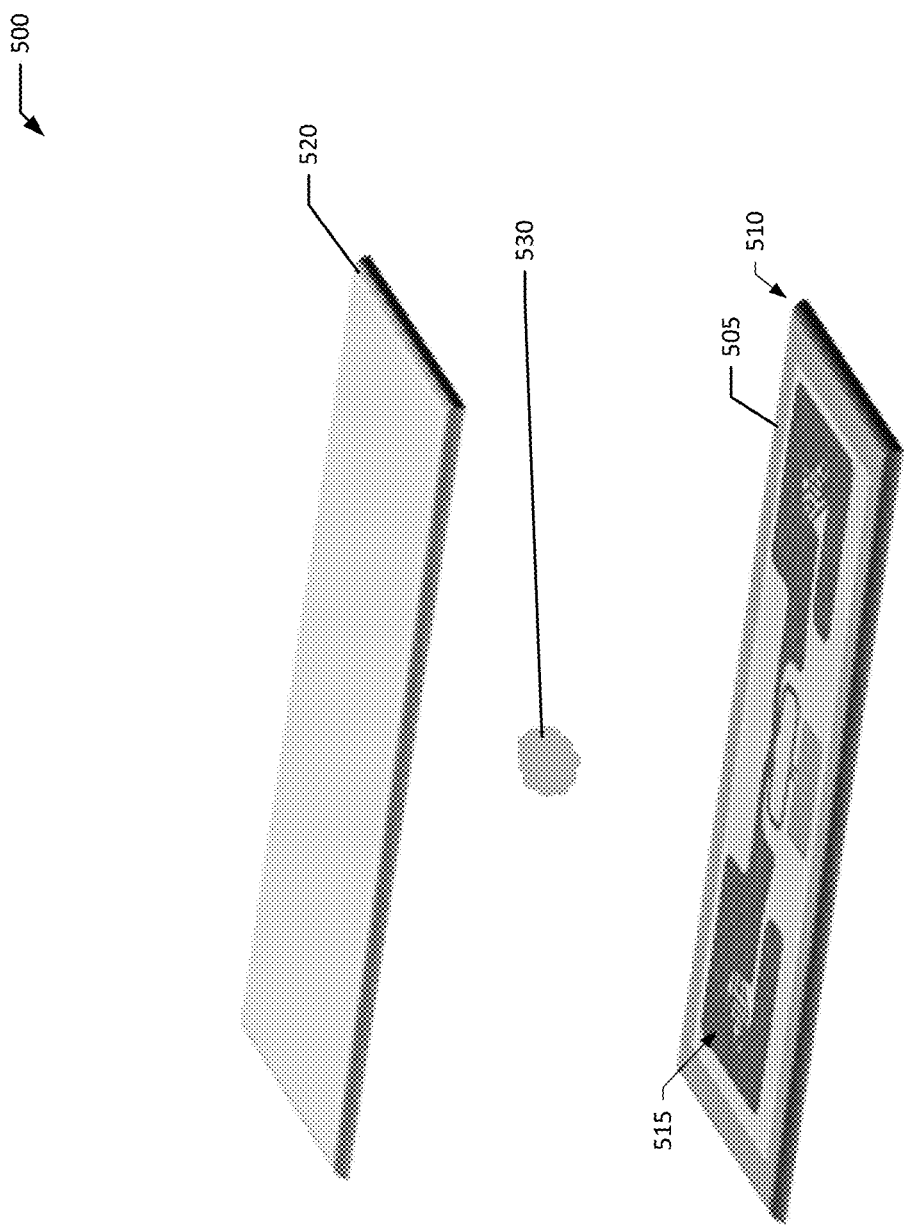
FIG. 9 is an expanded view of an RFID tag system according to an example embodiment of the present disclosure.

FIG. 9 is an expanded view of an RFID tag system 500 according to an example embodiment of the present disclosure. As shown in FIG. 9, the RFID tag system 500 may include an RFID inlay plate 510 having an RFID inlay 515 embedded on a substrate 505, a protection layer 520, and a dielectric material 530. As used herein, the RFID inlay 515 may refer to the components of an RFID tag system (e.g., RFID tag system 300/400), including an antenna, integrated circuit, electrodes, and gap between the electrodes, except for the dielectric material (e.g., dielectric material 130/230) and the substrate 505 (e.g., substrate 305/405). The protection layer 520 may be provided to protect the RFID inlay 515 (e.g., having an antenna, integrated circuit, first/second electrode, and gap) and the dielectric material 530. In some examples, the protection layer 520 may be made with an adhesive laminate. In other examples, the protection layer 520 may be made with any other suitable material. The dielectric material 530 may be similar to or same as the dielectric material described above (e.g., dielectric material 130/230).

Figure 10:
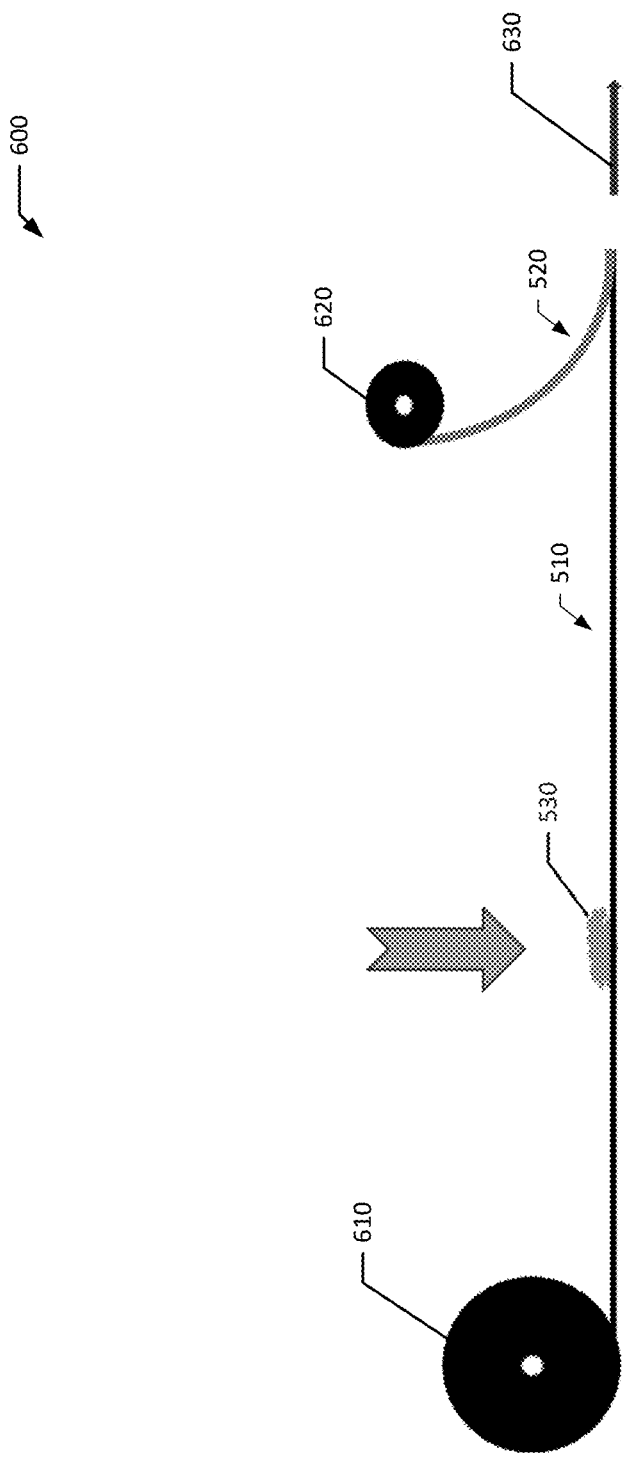
FIG. 10 is an example process of assembling the RFID tag system of FIG. 9.

FIG. 10 illustrates an example process of assembling the RFID tag system 500 of FIG. 9. As shown in FIG. 10, an RFID inlay roll 610 and a protection layer roll 620 may be provided. The RFID inlay roll 610 may be a rolled continuous film layer of a plurality of the RFID inlay plates 510. The protection layer roll 620 may be a rolled continuous film layer of the protection layer 520. In some examples, as the RFID inlay roll 610 is unrolled in a forward direction 630, the dielectric material 530 may be sprayed/applied to the RFID inlay plate 510 of the RFID inlay roll 610 (on the gap of the humidity or gas indicator). As the dielectric material 530 is sprayed/applied to the RFID inlay plates 510 of the RFID inlay roll 610, the RFID inlay roll 610 may be also unrolled to cover the RFID inlay plate 510 and the dielectric material 530 sprayed/applied on the RFID inlay plate 510. In some examples, as the assembled RFID tag systems 500 are pulled out in the forward direction 630, a cutter device may divide the assembled RFID tag systems 500 from each other in real time. In other examples, the cutter device may start dividing the assembled RFID tag systems 500 from each other after a certain number (e.g., 100, 200, 300) of the RFID tag systems 500 are assembled or after the RFID inlay roll 610 or the protection layer roll 620 is fully unrolled.

In some examples, the humidity or gas indicators 100, 200 and/or the RFID tag systems 300, 400, 500 may be used for a product/container having a host product that may be sensitive to the change in humidity or gas concentration or that may generate gas when the host product is in an abnormal condition. The humidity or gas indicators 100, 200 and/or the RFID tag systems 300, 400, 500 may be associated with the host product and/or the container to monitor a humidity or gas level change of the host product/container. For example, the humidity or gas indicators 100, 200 and/or the RFID tag systems 300, 400, 500 may be attached to the host product and/or the container, or at a place near the host product and/or the container. Examples of host products may include food stuffs, flowers, concrete, batteries, vaccines, drugs, medication, pharmaceuticals, cosmeceuticals, nutricosmetics, nutritional supplements, biological materials for industrial or therapeutic uses, medical devices, electrical devices, prophylactics, cosmetics, beauty aids, and perishable munitions and ordnance. In some examples, the capacitance of the humidity or gas indicators 100, 200, 330, 430, 450 may be read using a capacitance meter or multimeter (e.g., BK 878B).

EXAMPLES

Example 1

An example of capacitance change of humidity indicator and its response to change in humidity may be shown in Tables 1 and 2 below. In these examples, water reducible epoxy and PET were used for the dielectric material and substrate of the humidity or gas indicators, respectively.

TABLE 1

Capacitance change at room temperature, 40% RH after 72 hours

| Sample Conditions | Initial Sample (Room Temp., less than 40% RH) | Room Temp., 40% RH |
| --- | --- | --- |
| Avg. pF | 7.3 | 12.4 |

TABLE 2

Capacitance change at room temperature, 70% RH after 72 hours

| Sample Conditions | Initial Sample (no exposure to humidity) | Room Temp., 75% RH |
| --- | --- | --- |
| Avg. pF | 6 | 27.5 |

As shown in Table 1, when the humidity or gas indicators were placed in a chamber at room temperature, 40% RH for 72 hours, the average capacitance was changed from around 7.3 pF to around 12.4 pF. As shown in Table 2, when the humidity or gas indicators were placed in a chamber at room temperature, 75% RH for 72 hours, the average capacitance was changed from around 6 pF to around 27.5 pF. The results show that as the humidity increases, the capacitance of the humidity or gas indicators also increased.

Example 2

Another example of capacitance change of humidity or gas indicators according to change in humidity is shown in Table 3 below. In this example, OTTOPOL (e.g., neutralized polyacrylate) and PET were used for the dielectric material and substrate (e.g., OTTOPOL coated on PET) of the humidity or gas indicators, respectively. The humidity or gas indicators were placed in a chamber having a different humidity as shown in the table below. The capacitance of the humidity or gas indicators were measured after the humidity or gas indicators were placed in the chamber for 24 hours.

TABLE 3

Capacitance change at room temperature, after 24 hours

| | RH % | | |
| --- | --- | --- | --- |
| | 33 | 54 | 75 |
| Avg. pF | 11.72 | 15.67 | 17.83 |

As shown in Table 3, as the humidity increases (from 33% RH to 54% RH to 75% RH), the capacitance of the humidity or gas indicators also increased (from 11.72 pF to 15.67 pF to 17.83 pF).

Example 3

An example of capacitance change of humidity or gas indicators according to change in gas concentration ($NH_3$) is shown in Table 4 below. In this example, five sample humidity or gas indicators were used, where OTTOPOL (e.g., neutralized polyacrylate) and PET were used for the dielectric material and substrate (e.g., OTTOPOL coated on PET) of the humidity or gas indicators, respectively. Each of the five samples were placed in a chamber having a different ammonia concentration as shown in the table below. Other conditions (e.g., temperature, humidity) were the same. The capacitance of the sample humidity or gas indicators were measured after the samples were placed in the chamber for 24 hours.

TABLE 4

Capacitance change at room temperature, 82% RH after 24 hours according to the change in ammonia concentration

| Sample # | Ammonia (NH$_3$) Concentration, ppm | Capacitance (pF) |
|---|---|---|
| 1 | 0 | 15.5 |
| 2 | 100 | 150.1 |
| 3 | 1000 | 266.1 |
| 4 | 5000 | 755.4 |
| 5 | 260,000 | 2700 |

As shown in Table 4, when other conditions were the same (temperature, humidity, time), the capacitance of the humidity or gas indicators was increased as the ammonia concentration was increased.

Example 4

An example of capacitance change of humidity or gas indicators according to change in humidity and gas concentration (NH$_3$) is shown in Table 5 below. In this example, three sample humidity or gas indicators were used, where OTTOPOL (e.g., neutralized polyacrylate) and PET were used for the dielectric material and substrate (e.g., OTTOPOL coated on PET) of the humidity or gas indicators, respectively. Each of the three samples were placed in three different chambers, one by one. For example, each sample was placed in a first chamber having 40% RH for 24 hours, then in a second chamber having 82% RH for 24 hours, and then in a third chamber having 82% RH and ammonia (NH$_3$) concentration of 260,000 ppm for 24 hours. The temperature of the three chambers was the same (room temperature). The capacitance of the sample humidity or gas indicators were measured after the samples were pulled out of each chamber.

TABLE 5

Capacitance change according to the change in humidity and gas concentration

| Sample Conditions | Room Temp., 40% RH, no NH3 | Room Temp., 82% RH, no NH3 | Room Temp., 82% RH, NH$_3$ 260,000 ppm |
|---|---|---|---|
| Sample 1 | 5.6 pF | 15.5 pF | 2617 pF |
| Sample 2 | 7.8 pF | 18.1 pF | 2845 pF |
| Sample 3 | 6.4 pF | 16.6 pF | 2812 pF |

As shown in Table 5, there was a small change in capacitance when only the humidity was changed (around 10 pF), but there was a huge change in capacitance when the gas concentration was also changed (around a couple order of magnitude difference).

Embodiments

Various aspects of the subject matter described herein are set out in the following numbered embodiments:

Embodiment 1. An RFID tag system comprises: an antenna; an integrated circuit electrically connected to the antenna; and a humidity or gas indicator being electrically connected to the antenna and the integrated circuit; wherein the humidity or gas indicator comprising: a first electrode; a second electrode; a dielectric material; and a gap between the first electrode and the second electrode, at least a portion of the gap containing the dielectric material, wherein the dielectric material is configured to have a change in its dielectric constant responsive to exposure to an environmental stimulus, the environmental stimulus being at least one of humidity or the presence of a gas, wherein the change in the dielectric constant of the dielectric material changes a capacitance of the humidity or gas indicator, causing the integrated circuit to indicate the presence of the environmental stimulus.

Embodiment 2. The RFID tag system of claim 1, wherein the dielectric material comprises a material selected from the group consisting of polyol polymers, neutralized polymers, and combinations thereof.

Embodiment 3. The RFID tag system of embodiments 1-2, wherein the dielectric material comprises a material selected from the group consisting of PVA, PVP, PEG, acrylics, water reducible epoxy, cellulose, water soluble gum, PEG, hydrochromic ink, and combinations thereof.

Embodiment 4. The RFID tag system of embodiments 1-3, wherein the change in capacitance of the humidity or gas indicator occurs after exposure to a change in humidity or gas concentration above a first threshold change value for a first predetermined amount of time or less.

Embodiment 5. The RFID tag system of embodiments 1-4, wherein the first predetermined amount of time is 30 seconds or less.

Embodiment 6. The RFID tag system of embodiments 1-4, wherein the first predetermined amount of time is 1 hour or less.

Embodiment 7. The RFID tag system of embodiments 1-6, wherein the first electrode and the second electrode are in a comb shape and interleaved with each other.

Embodiment 8. The RFID tag system of embodiments 1-7, wherein the change in capacitance of the humidity or gas indicator is reversible.

Embodiment 9. The RFID tag system of embodiments 1-7, wherein the change in capacitance of the humidity or gas indicator is irreversible.

Embodiment 10. The RFID tag system of embodiments 1-9, wherein the integrated circuit is configured to detect a capacitance value or the change in capacitance of the humidity or gas indicator.

Embodiment 11. The RFID tag system of embodiments 1-10, further comprising a memory configured to record information indicating the detected change in capacitance of the humidity or gas indicator.

Embodiment 12. The RFID tag system of embodiments 1-11, further comprising an RFID reader configured to receive a communication from the integrated circuit or the memory indicating the detected change in capacitance of the humidity or gas indicator.

Embodiment 13. The RFID tag system of embodiments 1-12, wherein the integrated circuit is configured to transmit a notification to the RFID reader in response to detecting a capacitance value of the humidity or gas indicator equal to or greater than a first threshold capacitance value.

Embodiment 14. The RFID tag system of embodiment 13, wherein the first threshold capacitance value corresponds to a first humidity value in a range selected from the group consisting of from about 50% to about 55% RH, from about 55% to about 60% RH, from about 60% to about 65% RH, from about 65% to about 70% RH, from about 70% to about 75% RH, from about 75% to about 80% RH, from about 80% to about 85% RH, from about 85% to about 90% RH, and combinations thereof.

Embodiment 15. The RFID tag system of embodiment 13, wherein the first threshold capacitance value corresponds to an ammonia gas concentration value in a range of about 50 ppm to about 150 ppm.

Embodiment 16. The RFID tag system of embodiment 13, wherein the first threshold capacitance value corresponds to a carbon monoxide gas concentration value in a range of about 70 ppm to about 150 ppm.

Embodiment 17. The RFID tag system of embodiment 13, wherein the first threshold capacitance value corresponds to an electrolyte gas concentration value in a range of about 50 ppm to about 2,000 ppm.

Embodiment 18. The RFID tag system of embodiment 12, wherein the integrated circuit is configured to transmit a notification to the RFID reader in response to detecting a capacitance value of the humidity or gas indicator equal to or lower than a second threshold capacitance value.

Embodiment 19. The RFID tag system of embodiment 18, wherein the second threshold capacitance value corresponds to a second humidity value in a range selected from the group consisting of from about 10% to about 15% RH, from about 15% to about 20% RH, from about 20% to about 25% RH, from about 25% to about 30% RH, from about 30% to about 35% RH, from about 35% to about 40%, and combinations thereof.

Embodiment 20. The RFID tag system of embodiment 18, wherein the second threshold capacitance value corresponds to an atmosphere with an oxygen gas concentration value in a range of about 10% to 19.5% by volume.

Embodiment 21. The RFID tag system of embodiments 1-20, wherein the dielectric material is configured to change color after exposure to a change in humidity or gas concentration above a second threshold change value for a second predetermined amount of time or less.

Embodiment 22. The RFID tag system of embodiment 21, wherein the second predetermined amount of time is 30 seconds or less.

Embodiment 23. The RFID tag system of embodiment 21, wherein the second predetermined amount of time is 1 hour or less.

Embodiment 24. The RFID tag system of embodiments 1-23, further comprising a substrate on or in which the antenna, the integrated circuit, and/or the humidity or gas indicator are disposed, wherein the substrate comprises a paper or PET.

Embodiment 25. The RFID tag system of embodiments 1-24, wherein an area of the humidity or gas indicator covered by the dielectric material is less than 30% of the total size of the humidity or gas indicator.

Embodiment 26. The RFID tag system of embodiments 1-25, wherein the humidity or gas indicator is configured to change a capacitance value thereof in response to both the change in humidity and the change in gas concentration, wherein the integrated circuit is configured to differentiate whether the changed capacitance value is triggered by the change in humidity or the change in gas concentration.

Embodiment 27. The RFID tag system of embodiments 1-26, wherein the humidity or gas indicator is configured to serve as a humidity indicator, and the dielectric material is configured to have the change in its dielectric constant responsive to exposure to the humidity, wherein the RFID tag system further comprises: a gas indicator disposed being electrically connected to the antenna and the integrated circuit, wherein the gas indicator comprises: a third electrode, a fourth electrode, a second dielectric material, and a second gap between the third electrode and the fourth electrode, at least a portion of the second gap containing the second dielectric material, wherein the second dielectric material is configured to have a change in its dielectric constant responsive to exposure to the presence of gas, wherein the change in the dielectric constant of the second dielectric material changes a capacitance of the gas indicator, causing the integrated circuit to indicate the presence of the gas.

Embodiment 28. The RFID tag system of embodiment 27, wherein the gas indicator is calibrated using the humidity indicator.

Embodiment 29. A humidity- or gas-sensitive product, comprising: a host product and the humidity or gas indicator of any one of embodiments 1-28, wherein the humidity or gas indicator is associated with the host product to monitor the change in humidity or gas concentration of the host product.

Embodiment 30. The humidity- or gas-sensitive product of embodiment 29, wherein the host product comprises a product selected from the group consisting of food stuffs, flowers, concrete, batteries, vaccines, drugs, medication, pharmaceuticals, cosmeceuticals, nutricosmetics, nutritional supplements, biological materials for industrial or therapeutic uses, medical devices, electrical devices, prophylactics, cosmetics, beauty aids, and perishable munitions and ordnance.

As used herein, "about," "approximately," and "substantially" are understood to refer to numbers in a range of numerals, for example, the range of −10% to +10% of the referenced number, preferably −5% to +5% of the referenced number, more preferably −1% to +1% of the referenced number, most preferably −0.1% to +0.1% of the referenced number. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

Reference throughout the specification to "various aspects," "some aspects," "some examples," "other examples," "some cases," or "one aspect" means that a particular feature, structure, or characteristic described in connection with the aspect is included in at least one example. Thus, appearances of the phrases "in various aspects," "in some aspects," "certain embodiments," "some examples," "other examples," "certain other embodiments," "some cases," or "in one aspect" in places throughout the specification are not necessarily all referring to the same aspect. Furthermore, the particular features, structures, or characteristics illustrated or described in connection with one example may be combined, in whole or in part, with features, structures, or characteristics of one or more other aspects without limitation.

When the position relation between two parts is described using the terms such as "on," "above," "below," "under," and "next," one or more parts may be positioned between the two parts unless the terms are used with the term "immediately" or "directly." Similarly, as used herein, the terms "attachable," "attached," "connectable," "connected," or any similar terms may include directly or indirectly attachable, directly or indirectly attached, directly or indirectly connectable, and directly or indirectly connected.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

The terminology used herein is intended to describe particular embodiments only and is not intended to be limiting of the present disclosure. As used herein, the singular forms "a," "an," and "the" are intended to include the plural forms as well, unless otherwise indicated. It will be further understood that the terms "comprises" and/or "comprising," when used in this specification, specify the presence of stated features, integers, steps, operations, elements, and/or components, but they do not preclude the presence or addition of one or more other features, integers, steps, operations, elements, components, and/or groups thereof. As used herein, the term "at least one of X or Y" or "at least one of X and Y" should be interpreted as X, or Y, or X and Y.

It should be understood that various changes and modifications to the examples described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An RFID tag system comprising:
    an antenna;
    an integrated circuit electrically connected to the antenna; and
    a humidity and gas indicator being electrically connected to the antenna and the integrated circuit;
        wherein the humidity and gas indicator comprises:
            a first electrode;
            a second electrode;
            a dielectric material configured to have a first change in a dielectric constant of the dielectric material responsive to an exposure to humidity and to have a second change in the dielectric constant responsive to an exposure to a gas; and
            a gap between the first electrode and the second electrode, at least a portion of the gap containing the dielectric material,
        wherein the first change in the dielectric constant of the dielectric material causes a capacitance between the first electrode and the second electrode to change to a capacitance in a first predetermined range, and the second change in the dielectric constant of the dielectric material causes the capacitance between the first electrode and the second electrode to change to a capacitance in a second predetermined range,
        wherein the integrated circuit is configured to indicate a presence of humidity when the capacitance between the first electrode and the second electrode is in the first predetermined range and configured to indicate a presence of the gas when the capacitance between the first electrode and the second electrode is in the second predetermined range.
2. The RFID tag system of claim 1, wherein the dielectric material comprises a material selected from the group consisting of PVA, PVP, PEG, acrylics, water reducible epoxy, cellulose, water soluble gum, PEG, hydrochromic ink, and combinations thereof.
3. The RFID tag system of claim 1, wherein the second change in the dielectric constant occurs after exposure to a change in humidity above a first threshold change value for a first predetermined amount of time or less.
4. The RFID tag system of claim 1, wherein the first electrode and the second electrode are in a comb shape and interleaved with each other.
5. The RFID tag system of claim 1, wherein at least one of the first change and the second change in the dielectric constant is reversible.
6. The RFID tag system of claim 1, further comprising:
    a memory configured to record information indicating detected changes in capacitance values of the humidity and gas indicator; and
    an RFID reader configured to receive a communication from the integrated circuit or the memory indicating the detected changes in capacitance values.
7. The RFID tag system of claim 6, wherein the integrated circuit is configured to transmit a notification to the RFID reader in response to detecting a capacitance value of the humidity and gas indicator equal to or greater than a first threshold capacitance value.
8. The RFID tag system of claim 7, wherein the first threshold capacitance value corresponds to a first humidity value in a range selected from the group consisting of from about 50% to about 55% RH, from about 55% to about 60% RH, from about 60% to about 65% RH, from about 65% to about 70% RH, from about 70% to about 75% RH, from about 75% to about 80% RH, from about 80% to about 85% RH, from about 85% to about 90% RH, and combinations thereof.
9. The RFID tag system of claim 7, wherein the first threshold capacitance value corresponds to:
    an ammonia gas concentration value in a range of about 50 ppm to about 150 ppm; or
    a carbon monoxide gas concentration value in a range of about 70 ppm to about 150 ppm.
10. The RFID tag system of claim 7, wherein the first threshold capacitance value corresponds to an electrolyte gas concentration value in a range of about 50 ppm to about 2,000 ppm.
11. The RFID tag system of claim 6, wherein the integrated circuit is configured to transmit a notification to the RFID reader in response to detecting a capacitance value of the humidity and gas indicator equal to or lower than a second threshold capacitance value.
12. The RFID tag system of claim 11, wherein the second threshold capacitance value corresponds to:
    a second humidity value in a range selected from the group consisting of from about 10% to about 15% RH, from about 15% to about 20% RH, from about 20% to about 25% RH, from about 25% to about 30% RH, from about 30% to about 35% RH, from about 35% to about 40%, and combinations thereof, or
    an atmosphere with an oxygen gas concentration value in a range of about 10% to 19.5% by volume.
13. The RFID tag system of claim 1, wherein the dielectric material is configured to change color after exposure to a change in humidity or gas concentration above a second threshold change value for a second predetermined amount of time or less.
14. The RFID tag system of claim 1, further comprising a substrate on or in which the antenna, the integrated circuit, and the humidity and gas indicator are disposed, wherein the substrate comprises a paper, cloth, or plastic.

15. A humidity- or gas-sensitive product, comprising:
a host product; and
the RFID tag system of claim 1,
wherein the RFID tag is associated with the host product and communicates information indicating exposure of the host product to a change in humidity or gas concentration.

16. The RFID tag system of claim 1, wherein the first change in the dielectric constant occurs after exposure to a change in gas concentration above a first threshold change value for a first predetermined amount of time or less.

17. The RFID tag system of claim 1, wherein the first change in the dielectric constant occurs after exposure to a change in gas concentration above a first threshold change value for at least a first predetermined amount of time.

18. The RFID tag system of claim 1, wherein the second change in the dielectric constant occurs after exposure to a change in humidity above a first threshold change value for at least a first predetermined amount of time.

* * * * *